United States Patent
Topgaard et al.

(10) Patent No.: US 9,995,812 B2
(45) Date of Patent: Jun. 12, 2018

(54) ANALYSIS FOR QUANTIFYING MICROSCOPIC DIFFUSION ANISOTROPY

(71) Applicant: CR Development AB, Lund (SE)

(72) Inventors: Daniel Topgaard, Lund (SE); Samo Lasic, Lund (SE); Markus Nilsson, Oxie (SE)

(73) Assignee: CR Development AB, Lund (SE)

(*) Notice: Subject to any disclaimer, the term of this patent is extended or adjusted under 35 U.S.C. 154(b) by 679 days.

(21) Appl. No.: 14/398,272

(22) PCT Filed: May 3, 2013

(86) PCT No.: PCT/SE2013/050493
§ 371 (c)(1),
(2) Date: Oct. 31, 2014

(87) PCT Pub. No.: WO2013/165313
PCT Pub. Date: Nov. 7, 2013

(65) Prior Publication Data
US 2015/0130458 A1    May 14, 2015

Related U.S. Application Data

(60) Provisional application No. 61/642,589, filed on May 4, 2012.

(30) Foreign Application Priority Data

May 4, 2012   (SE) ........................................ 1250453

(51) Int. Cl.
G01R 33/56    (2006.01)
G01R 33/563    (2006.01)
G01N 24/08    (2006.01)

(52) U.S. Cl.
CPC ....... G01R 33/56341 (2013.01); G01N 24/08 (2013.01); G01R 33/56 (2013.01); G01R 33/56308 (2013.01); G01N 24/081 (2013.01)

(58) Field of Classification Search
CPC .............. G01R 33/56341; G01R 33/56; G01R 33/56308; G01N 24/08; G01N 24/081
See application file for complete search history.

(56) References Cited

U.S. PATENT DOCUMENTS 6,288,540 B1    9/2001  Chert et al.
6,992,484 B2    1/2006  Frank
(Continued)

FOREIGN PATENT DOCUMENTS

WO    WO-2011161683 A1    12/2011

OTHER PUBLICATIONS

Basser, Peter J. et al. "MR Diffusion Tensor Spectroscopy and Imaging." *Biophysical Journal*, vol. 66 (Jan. 1994): 259-267.
(Continued)

*Primary Examiner* — Clayton E Laballe
*Assistant Examiner* — Ruifeng Pu
(74) *Attorney, Agent, or Firm* — Harness, Dickey & Pierce, P.L.C.

(57) ABSTRACT

The present invention describes a method for quantifying microscopic diffusion anisotropy and/or mean diffusivity in a material by analysis of echo attenuation curves acquired with two different gradient modulations schemes, wherein one gradient modulation scheme is based on isotropic diffusion weighting and the other gradient modulation scheme is based on non-isotropic diffusion weighting, and wherein the method comprises analyzing by comparing the signal decays of the two acquired echo attenuation curves.

13 Claims, 2 Drawing Sheets

(56) References Cited

U.S. PATENT DOCUMENTS

| | | | |
|---|---|---|---|
| 7,411,394 | B2 | 8/2008 | Huang |
| 7,643,863 | B2 | 1/2010 | Basser et al. |
| 2005/0007100 | A1 | 1/2005 | Basser et al. |
| 2005/0068031 | A1 | 3/2005 | Frank |
| 2006/0241375 | A1* | 10/2006 | Van Den Brink ............... G01R 33/56341 600/410 |
| 2006/0261808 | A1 | 11/2006 | Huang |
| 2009/0058419 | A1* | 3/2009 | Kabasawa ........ G01R 33/56341 324/309 |
| 2010/0033182 | A1* | 2/2010 | Ozarslan .......... G01R 33/56341 324/309 |
| 2012/0049845 | A1* | 3/2012 | Bito ..................... G01R 33/485 324/309 |
| 2012/0068699 | A1* | 3/2012 | Horkay ................... A61B 5/055 324/300 |
| 2013/0106415 | A1 | 5/2013 | Cohen et al. |
| 2015/0115957 | A1* | 4/2015 | Topgaard ......... G01R 33/56341 324/309 |
| 2016/0231410 | A1* | 8/2016 | Warfield ................ A61B 5/055 |
| 2016/0356873 | A1* | 12/2016 | Topgaard ............... A61B 5/055 |

OTHER PUBLICATIONS

Basser, Peter J. and Carlo Pierpaoli. "Microstructural and Physiological Features of Tissues Elucidated by Quantitative-Diffusion-Tensor MRI." *Journal of Magnetic Resonance*, series B, vol. 111 (1996): 209-219.

Beaulieu, Christian. "The basis of anisotropic water diffusion in the nervous system—a technical review." *NMR in Biomedicine*, vol. 15 (2002): 435-455.

Callaghan, P.T. and I. Furó. "Diffusion-diffusion correlation and exchange as a signature for local order and dynamics." *Journal of Chemical Physics*, vol. 120, No. 8 (Feb. 2004): 4032-4038.

Callaghan, P.T. and M.E. Komlosh. "Locally anisotropic motion in a macroscopically isotropic system: displacement correlations measured using double pulsed gradient spin-echo NMR." *Magnetic Resonance in Chemistry*, vol. 40 (2002): S15-S19.

Callaghan, P.T. and O. Soderman. "Examination of the Lamellar Phase of Aerosol OT/Water Using Pulsed Field Gradient Nuclear Magnetic Resonance." *Journal of Physical Chemistry*, vol. 87 (1983): 1737-1744.

De Graaf, Robin A. et al. "Single-Shot Diffusion Trace $^1$H NMR Spectroscopy." *Magnetic Resonance in Medicine*, vol. 45 (2001): 741-748.

Frisken, Barbara J. "Revisiting the method of cumulants for the analysis of dynamic light-scattering data." *Applied Optics*, vol. 40, No. 24 (Aug. 2001): 4087-4091.

Hubbard, Penny L. et al. "Orientational Anisotropy in the Polydomain Lamellar Phase of a Lyotropic Liquid Crystal." *Langmuir*, vol. 22 (2006): 3999-4003.

Hubbard, Penny L. et al. "A Study of Anisotropic Water Self-Diffusion and Defects in the Lamellar Mesophase." *Langmuir*, vol. 21 (2005): 4340-4346.

Hürlimann, M.D. et al. "Restricted Diffusion in Sedimentary Rocks. Determination of Surface-Area-to-Volume Ration and Surface Relaxivity." *Journal of Magnetic Resonance*, series A, vol. 111 (1994): 169-178.

Jensen, Jens H. and Joseph A. Helpern. "MRI Quantification of Non-Gaussian Water Diffusion by Kurtosis Analysis." *NMR Biomedicine*, vol. 23, No. 7 (Aug. 2010): 698-710.

Mariette, François et al. "$^1$H NMR Diffusometry Study of Water in Casein Dispersions and Gels." *Journal of Agricultural Food Chemistry*, vol. 50 (2002): 4295-4302.

Mitra, Partha P. "Multiple wave-vector extensions of the NMR pulsed-field-gradient spin-echo diffusion measurement." *Physical Review B*, vol. 51 No. 21 (Jun. 1995): 15074-15078.

Mori, Susumu and Peter C.M. van Zijl. "Diffusion Weighting by the Trace of the Diffusion Tensor within a Single Scan." *Magnetic Resonance in Medicine*, vol. 33 (1995): 41-52.

Moseley, Michael E. et al. "Anisotropy in Diffusion-Weighted MRI." *Magnetic Resonance in Medicine*, vol. 19 (1991): 321-326.

Shemesh, Noam and Yoram Cohen. "Microscopic and Compartment Shape Anisotropies in Gray and White Matter Revealed by Angular Bipolar Double-PFG MR." *Magnetic Resonance in Medicine*, vol. 65 (2011): 1216-1227.

Shemesh, Noam et al. "Probing Microscopic Architecture of Opaque Heterogeneous Systems Using Double-Pulsed-Field-Gradient NMR." *Journal of the American Chemical Society*, vol. 133 (2011): 6028-6035.

Topgaard, Daniel et al. "Restricted Self-Diffusion of Water in a Highly Concentrated W/O Emulsion Studied Using Modulated Gradient Spin-Echo NMR." *Journal of Magnetic Resonance*, vol. 156 (2002): 195-201.

Topgaard, Daniel and Olle Söderman. "Self-Diffusion in Two-and Three-Dimensional Powders of Anisotropic Domains: An NMR Study of the Diffusion of Water in Cellulose and Starch." *The Journal of Physical Chemistry B*, vol. 106, No. 46 (Nov. 2002): 11887-11892.

Valette, Julien et al. "A New Sequence for Single-Shot Diffusion-Weighted NMR Spectroscopy by the Trace of the Diffusion Tensor." *Magnetic Resonance in Medicine*, vol. 68 (2012): 1705-1712.

Baloch, Sajjad et al. "Quantification of Brain Maturation and Growth Patterns in C57BL/6J Mice via Computational Neuroanatomy of Diffusion Tensor Images." *Cerebral Cortex* 19:3 (2008) 675-687.

Extended European Search Report dated Jun. 24, 2016 issued in corresponding European Application No. 15197166.0.

Basser, Peter J. "Inferring Microstructural Features and the Physiological State of Tissues from Diffusion-Weighted Images." *NMR in Biomedicine*, vol. 8 (1995): 333-344.

Assemlal, Haz-Edine, et al. "Recent advances in diffusion MRI modeling: Angular and radial reconstruction." *Medical Image Analysis*, vol. 15 (2011): 369-396.

Extended European Search Report dated Jun. 24, 2016 issued in corresponding European Application No. 13785201.8.

International Search Report PCT/ISA/210 for International Application No. PCT/SE2013/050493 dated Aug. 28, 2013.

Komlosh et al. "Detection of microscopic anisotropy in gray matter and in a novel tissue phantom using double Pulsed Gradient Spin Echo MR", Journal of magnetic resonance, USA, Nov. 2007, vol. 189, nr. 1, p. 38-45.

Komlosh et al. "Observation of microscopic diffusion anisotropy in the spinal cord using double-pulsed gradient spin echo MRI", Magnetic resonance in medicine, USA, Apr. 2008, vol. 59, nr. 4, p. 803-809.

Lawrenz et al. "A tensor model and measures of microscopic anisotropy for double-wave-vector diffusion-weighting experiments with long mixing times", Journal of Magnetic Resonance, USA, Jan. 2010, vol. 202, nr. 1, p. 43-56.

Lawrenz et al. "Detection of Microscopic Diffusion Anisotropy on a Whole-Body MR System With Double Wave Vector Imaging", Magnetic Resonance in Medicine, USA, Nov. 2011, vol. 66, nr. 5, p. 1405-1415.

Lawrenz et al. "Double-wave-vector diffusion-weighting experiments with multiple concatenations at long mixing times", Journal of Magnetic Resonance, USA: Sep. 2010, vol. 206, nr. 1, p. 112-119.

Bourne et al, "Microscopic diffusion anisotropy in fomalin fixed prostate tissue: Preliminary findings", Magnetic resonance in medicine, USA, Dec. 2012, vol. 68, nr. 6, p. 1943-1948.

Shemesh et al. "Observation of restricted diffusion in the presence of a free diffusion compartment: single- and double-PFG experiments", Journal of Magnetic Resonance, USA, Oct. 2009, vol. 200, nr. 2, p. 214-225.

Shemesh et al. "The effect of experimental parameters on the signal decay in double-PGSE experiments: negative diffractions and enhancement of structural information", Journal of Magnetic Resonance, USA, Dec. 2008, vol. 195, nr. 2, p. 153-161.

Jespersen et al. "Determination of Axonal and Dendritic Orientation Distributions Within the Developing Cerebral Cortex by Diffusion Tensor Imaging", IEEE Transactions on Medical Imaging, USA, Jan. 2012, vol. 31, nr. 1, p. 16-32.

(56) References Cited

OTHER PUBLICATIONS

Finsterbusch "Numerical simulations of short-mixing-time double-wave-vector diffusion-weighting experiments with multiple concatenations on whole-body MR systems", Journal of Magnetic Resonance, USA, Dec. 2010, vol. 207, nr. 2, p. 274-282.

* cited by examiner

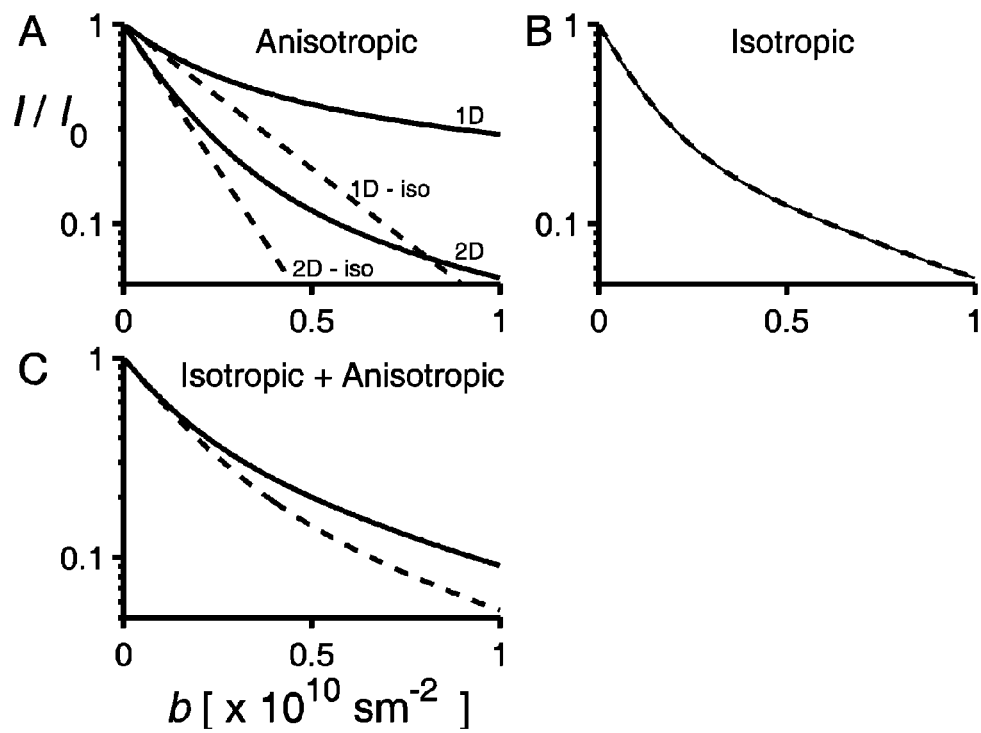
Fig. 1A-C
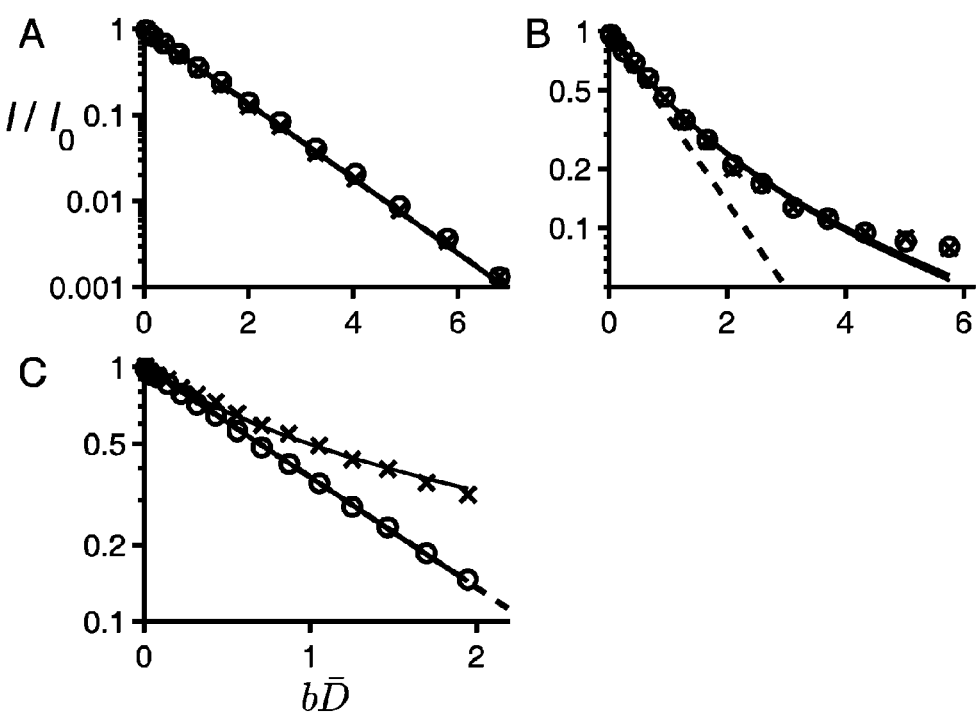
Fig. 2A-C

ANALYSIS FOR QUANTIFYING MICROSCOPIC DIFFUSION ANISOTROPY

This application is the national phase under 35 U.S.C. § 371 of PCT International Application No. PCT/SE2013/050493 which has an International filing date of May 3, 2013, which claims priority to Swedish patent application number SE 1250453-6 filed May 4, 2012 and U.S. Provisional application No. 61/642,589 filed May 4, 2012; the entire contents of each of which are hereby incorporated by reference.

FIELD OF THE INVENTION

The present invention relates to a method for quantifying microscopic diffusion anisotropy in a material with magnetic resonance imaging or nuclear magnetic resonance spectroscopy.

TECHNICAL BACKGROUND

Molecular self-diffusion measured with NMR (nuclear magnetic resonance) (Callaghan, 2011 in "Translational Dynamics & Magnetic Resonance" (Oxford, Oxford University Press); Price, 2009 in "NMR Studies of Translational Motion" (Cambridge, Cambridge University Press)) is used to non-invasively study the morphology of the water-filled pore space of a wide range of materials, e.g., rocks (Hürlimann et al., 1994 "Restricted diffusion in sedimentary rocks. Determination of surface-area-to-volume ratio and surface relaxivity". J Magn Reson A 111, 169-178), emulsions (Topgaard et al., 2002, "Restricted self-diffusion of water in a highly concentrated W/O emulsion studied using modulated gradient spin-echo NMR". J Magn Reson 156, 195-201.), and cheese (Mariette et al., 2002, "$^1$H NMR diffusometry study of water in casein dispersions and gels". J Agric Food Chem 50, 4295-4302.).

Anisotropy of the pore structure renders the water self-diffusion anisotropic, a fact that is utilized for three-dimensional mapping of nerve fiber orientations in the white matter of the brain where the fibers have a preferential direction on macroscopic length scales (Basser et al., 1994, "MR diffusion tensor spectroscopy and imaging". Biophys J 66, 259-267; Beaulieu, 2002, "The basis of anisotropic water diffusion in the nervous system—a technical review". NMR Biomed 15, 435-455; Moseley et al., 1991, "Anisotropy in diffusion-weighted MRI". Magn Reson Med 19, 321-326.). The degree of the macroscopic diffusion anisotropy is often quantified by the non-dimensional fractional anisotropy index (Basser and Pierpaoli, 1996, "Microstructural and physiological features of tissues elucidated by quantitative-diffusion-tensor MRI". J Magn Reson B 111, 209-219.).

Also microscopic anisotropy in a globally isotropic material can be detected with diffusion NMR, originally through the characteristic curvature observed in the echo attenuation of conventional single-PGSE (pulsed gradient spin-echo) techniques (Callaghan and Söderman, 1983, in "Examination of the lamellar phase of aerosol OT/water using pulsed field gradient nuclear magnetic resonance". J Phys Chem 87, 1737-1744; Topgaard and Söderman, 2002, in "Self-diffusion in two- and three-dimensional powders of anisotropic domains: An NMR study of the diffusion of water in cellulose and starch". J Phys Chem B 106, 11887-11892.) and, more recently, by using double-PGSE approaches in which the NMR signal is encoded for displacements over two separate time periods (Mitra, 1995, in "Multiple wave-vector extension of the NMR pulsed-field-gradient spin-echo diffusion measurement". Phys Rev B 51, 15074-15078.). The presence of microscopic anisotropy can be inferred by comparing echo attenuation data obtained with collinear and orthogonal displacement encoding (Callaghan and Komlosh, 2002, in "Locally anisotropic motion in a macroscopically isotropic system: displacement correlations measured using double pulsed gradient spin-echo NMR". Magn Reson Chem 40, S15-S19.; Komlosh et al., 2007, in "Detection of microscopic anisotropy in gray matter and in novel tissue phantom using double Pulsed Gradient Spin Echo MR". J Magn Reson 189, 38-45.; Komlosh et al., 2008, in "Observation of microscopic diffusion anisotropy in the spinal cord using double-pulsed gradient spin echo MRI". Magn Reson Med 59, 803-809.), by the characteristic signal modulations observed when varying the angle between the directions of displacement encoding (Mitra, 1995, in "Multiple wave-vector extension of the NMR pulsed-field-gradient spin-echo diffusion measurement". Phys Rev B 51, 15074-15078.; Shemesh et al., 2011, in "Probing Microscopic Architecture of Opaque Heterogeneous Systems Using Double-Pulsed-Field-Gradient NMR". J Am Chem Soc 133, 6028-6035, and "Microscopic and Compartment Shape Anisotropies in Gray and White Matter Revealed by Angular Bipolar Double-PFG MR". Magn Reson Med 65, 1216-1227.), or by a two-dimensional correlation approach (Callaghan and Furó, 2004, in "Diffusion-diffusion correlation and exchange as a signature for local order and dynamics". J Chem Phys 120, 4032-4038; Hubbard et al., 2005, 2006, in "A study of anisotropic water self-diffusion and defects in the lamellar mesophase". Langmuir 21, 4340-4346, and "Orientational anisotropy in polydomain lamellar phase of a lyotropic liquid crystal". Langmuir 22, 3999-4003.).

In typical diffusion magnetic resonance imaging (MRI) experiments, only a voxel average anisotropy can be detected. Detection of microscopic anisotropy in a globally isotropic material through the characteristic echo attenuation curve in conventional single-PGSE techniques demands high diffusion weighting, often not feasible in clinical applications, and suffers from very low sensitivity to microscopic anisotropy. Information about microscopic anisotropy is further hindered in such experiments by possible isotropic diffusion contributions to the echo attenuation which are superposed to anisotropic contributions. The low sensitivity to microscopic anisotropy is the main pitfall also in analysis of data from double PGSE experiments.

The present techniques are not adequately sensitive to microscopic anisotropy and are not best suited for clinical applications. Highly sensitive techniques to detect microscopic anisotropy, feasible for clinical applications, are thus needed. Furthermore, there is a need for a robust and fast data analysis approach allowing for an unambiguous quantification of microscopic anisotropy associated with a simple but concise parameter for its quantification. One aim of the present invention is to provide a new analysis method along with the novel parameter, microscopic fractional anisotropy (μFA), providing a robust, fast and highly sensitive means for quantifying microscopic anisotropy, which is suitable in non-clinical and in clinical applications alike.

SUMMARY OF THE INVENTION

The stated purpose above is achieved by a method for quantifying microscopic diffusion anisotropy and/or mean diffusivity in a material by analysis of echo attenuation curves acquired with two different gradient modulations schemes, wherein one gradient modulation scheme is based on isotropic diffusion weighting and the other gradient modulation scheme is based on non-isotropic diffusion weighting, and wherein the method comprises analyzing by comparing the signal decays of the two acquired echo attenuation curves.

The present analysis is highly sensitive to microscopic anisotropy independent of the particular choice of the isotropic diffusion weighting protocol. The analysis allows for a robust and fast quantification of microscopic anisotropy applicable in non-clinical and in clinical applications alike.

The analysis could be applied in combination with multi-dimensional (2D, 3D . . . ) correlation MR experiments to quantify microscopic anisotropy of different diffusion components. The analysis could also be applied in combination with other NMR or MRI methods. Therefore, according to one specific embodiment of the present invention the method is performed in an NMR and/or MRI method or experiment, or in a combination with another NMR or MRI method. For example, with an additional isotropic-weighted experiment, the analysis could be combined with the diffusion tensor and/or diffusion kurtosis measurement to provide additional information about morphology and microscopic anisotropy as well as anisotropic orientation dispersion. The analysis can be used to facilitate and strengthen the interpretation of diffusion tensor and diffusion kurtosis measurements in vivo. For example, the analysis can provide information on the degree of anisotropy and on multi-exponential signal decays detected in kurtosis tensor measurements by attributing kurtosis to different isotropic and/or anisotropic diffusion contributions. The characterization of any pathology involving the change in microscopic anisotropy will benefit from the improvements that our method introduces.

BRIEF DESCRIPTION OF THE DRAWINGS

FIG. 1A-C show schematic representations of signal decays vs. b for isotropic (dashed line) and non-isotropic (solid line) diffusion weighting for different types of materials. The inset A depicts signal attenuation curves in case of anisotropic materials with 1D or 2D curvilinear diffusion. The attenuation curves are multi-exponential for non-isotropic diffusion weighting, while they are mono-exponential for isotropic diffusion weighting. The deviation between the attenuation curves for isotropic and non-isotropic diffusion weighting provides a measure of anisotropy. The inset B depicts an example of isotropic material with several apparent diffusion contributions resulting in identical and multi-exponential signal attenuation curves for isotropic and non-isotropic diffusion weighting. The inset C depicts an example of material with a mixture of isotropic and anisotropic components resulting in multi-exponential signal decays for both isotropic and non-isotropic diffusion weighting, while the deviation between the attenuation curves for isotropic and non-isotropic diffusion weighting provides a measure of anisotropy.

FIG. 2A-C show experimental results with analysis for different types of materials. Experimental results for isotropic (circles) and for non-isotropic (crosses) diffusion weighting are shown in all the insets. Experimental results and analysis are shown for a sample with free isotropic diffusion (inset A), for a sample with restricted isotropic diffusion (inset B) and for a sample with high degree of anisotropy (inset C).

BACKGROUND TO THE ANALYSIS METHOD ACCORDING TO THE PRESENT INVENTION

Figure 3A:
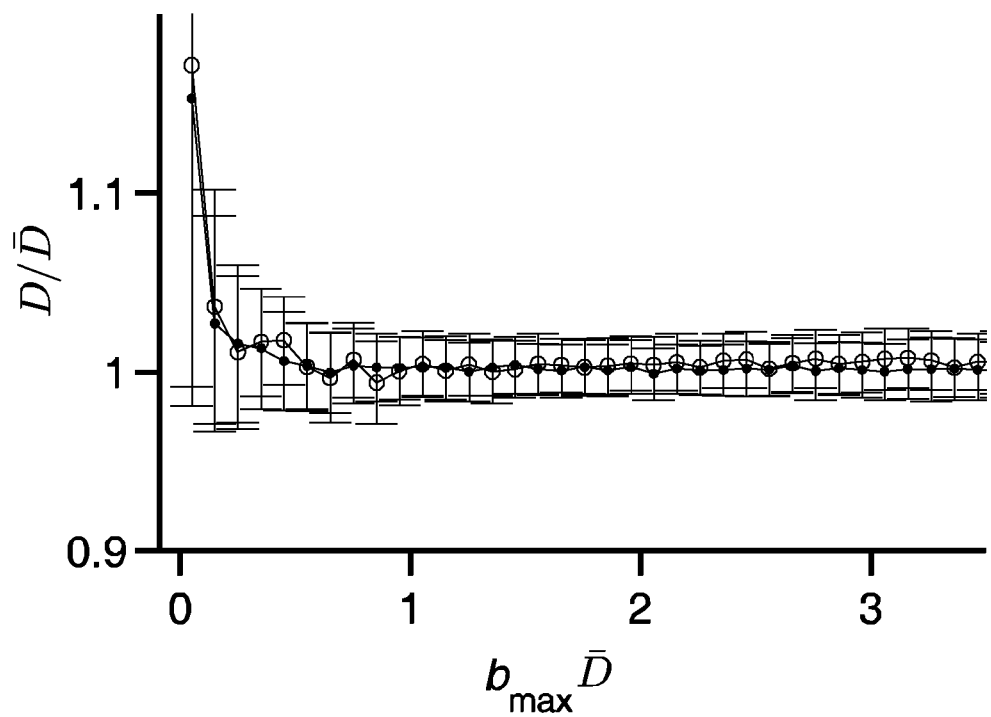
FIGS. 3A and 3B show a Monte-Carlo error analysis for the investigation of systematic deviations and precision as a function of the range of diffusion weighting b for estimating the degree of micro-anisotropy with the disclosed analytical method.

Below there will be disclosed one possible method for isotropic diffusion weighting as a background to the analysis method according to the present invention. It is important to understand that this is only given as an example and as a background for the isotropic diffusion weighting. The analysis method according to the present invention is of course not limited to this route or method. Fact is that all possible diffusion weighting methods involving one part (gradient modulation scheme) for isotropic diffusion weighting and one other part for the non-isotropic diffusion weighting are possible starting points, and thus pre-performed methods, for the analysis method according to the present invention.

Assuming that spin diffusion in a microscopically anisotropic system can locally be considered a Gaussian process and therefore fully described by the diffusion tensor D(r), the evolution of the complex transverse magnetization m(r,t) during a diffusion encoding experiment is given by the Bloch-Torrey equation. Note that the Bloch-Torrey equation applies for arbitrary diffusion encoding schemes, e.g. pulse gradient spin-echo (PGSE), pulse gradient stimulated echo (PGSTE) and other modulated gradient spin-echo (MGSE) schemes. Assuming uniform spin density and neglecting relaxation, the magnetization evolution is given by $$\frac{\partial m(r,t)}{\partial t} = -i\gamma g(t) \cdot r m(r,t) + \nabla \cdot [D(r) \cdot \nabla m(r,t)], \quad (1)$$

where $\gamma$ is the gyromagnetic ratio and g(t) is the time dependent effective magnetic field gradient vector. The NMR signal is proportional to the macroscopic transverse magnetization $$M(t) = \frac{1}{V} \int_V m(r,t) dr. \quad (2)$$

If during the experiment each spin is confined to a domain characterized by a unique diffusion tensor D, the macroscopic magnetization is a superposition of contributions from all the domains with different D. Evolution of each macroscopic magnetization contribution can thus be obtained by solving Eqs. (1, 2) with a constant and uniform D. The signal magnitude contribution at the echo time $t_E$ is given by $$I(t_E) = I_0 \exp\left(-\int_0^{t_E} q^T(t) \cdot D \cdot q(t) dt\right) \quad (3)$$
$$= I_0 \exp\left(-q^2 \int_0^{t_E} F(t)^2 \hat{q}^T(t) \cdot D \cdot \hat{q}(t) dt\right),$$

where $I_0$ is the signal without diffusion encoding, g=0, and q(t) is the time-dependent dephasing vector $$q(t) = \gamma \int_0^t g(t') dt' = qF(t)\hat{q}(t), \quad (4)$$

defined for the interval $0<t<t_E$. The dephasing vector in Eqs. (3) and (4) is expressed in terms of its maximum magnitude q, the time-dependent normalized magnitude $|F(t)|\leq 1$ and a time-dependent unit direction vector $\hat{q}(t)$. Note that in spin-echo experiments, the effective gradient g(t) comprises the effect of gradient magnitude reversal after each odd 180° radio frequency (RF) pulse in the sequence. Eq. (3) assumes that the condition for the echo formation $q(t_E)=0$ is fulfilled, which implies $F(t_E)=0$. In general there might be several echoes during an NMR pulse sequence.

The echo magnitude (3) can be rewritten in terms of the diffusion weighting matrix, $$b = q^2 \int_0^{t_E} F(t)^2 \hat{q}(t) \cdot \hat{q}^T(t) \, dt, \tag{5}$$

as $$I(t_E) = I_0 \exp(-b:D) = I_0 \exp\left(-\sum_i \sum_j b_{ij} D_{ij}\right). \tag{6}$$

Integral of the time-dependent waveform $F(t)^2$ defines the effective diffusion time, $t_d$, for an arbitrary diffusion encoding scheme in a spin-echo experiment $$t_d = \int_0^{t_E} F(t)^2 \, dt. \tag{7}$$

In the following we will demonstrate that even for a single echo sequence, gradient modulations g(t) can be designed to yield isotropic diffusion weighting, invariant under rotation of D, i.e. the echo attenuation is proportional to the isotropic mean diffusivity, $$\overline{D} = tr(D)/3 = (D_{xx} + D_{yy} + D_{zz})/3. \tag{8}$$

In view of what is disclosed above, according to one specific embodiment of the present invention, the isotropic diffusion weighting is invariant under rotation of the diffusion tensor D.

According to the present invention, one is looking for such forms of dephasing vectors $F(t)\hat{q}(t)$, for which $$\int_0^{t_E} F(t)^2 \hat{q}^T(t) \cdot D \cdot \hat{q}(t) \, dt = t_d \overline{D} \tag{9}$$

is invariant under rotation of D. If diffusion tenor D is expressed as a sum of its isotropic contribution, $\overline{D}I$, where I is the identity matrix, and the anisotropic contribution, i.e. the deviatoric tensor $D^A$, so that $D = \overline{D}I + D^A$, the isotropic diffusion weighing is achieved when the condition $$\int_0^{t_E} F(t)^2 \hat{q}^T(t) \cdot D^A \cdot \hat{q}(t) \, dt = 0 \tag{10}$$

is fulfilled.

In spherical coordinates, the unit vector $\hat{q}(t)$ is expressed by the inclination $\zeta$ and azimuth angle $\psi$ as $$\hat{q}^T(t) = \{\hat{q}_x(t), \hat{q}_y(t), \hat{q}_z(t)\} = \{\sin\zeta(t)\cos\psi(t), \sin\zeta(t)\sin\psi(t), \cos\zeta(t)\}. \tag{11}$$

The symmetry of the diffusion tensor, $D=D^T$, gives $$\hat{q}^T \cdot D \cdot \hat{q} = \hat{q}_x^2 D_{xx} + \hat{q}_y^2 D_{yy} + \hat{q}_z^2 D_{zz} + 2\hat{q}_x\hat{q}_y D_{xy} + 2\hat{q}_x\hat{q}_z D_{xz} + 2\hat{q}_y\hat{q}_z D_{yz} \tag{12}$$

or expressed in spherical coordinates as $$\hat{q}^T \cdot D \cdot \hat{q} = \sin^2\zeta\cos^2\psi D_{xx} + \sin^2\zeta\sin^2\psi D_{yy} + \cos^2\zeta D_{zz} + 2\sin\zeta\cos\psi\sin\zeta\sin\psi D_{xy} + 2\sin\zeta\cos\psi\cos\zeta D_{xz} + 2\sin\zeta\sin\psi\cos\zeta D_{yz}. \tag{13}$$

Equation (13) can be rearranged to $$\hat{q} \cdot D \cdot \hat{q} = \overline{D} + \frac{3\cos^2\zeta - 1}{2}(D_{zz} - \overline{D}) + \sin^2\zeta\left[\frac{D_{xx} - D_{yy}}{2}\cos(2\psi) + D_{xy}\sin(2\psi)\right] + \sin(2\zeta)(D_{xz}\cos\psi + D_{yz}\sin\psi) \tag{14}$$

The first term in Eq. (14) is the mean diffusivity, while the remaining terms are time-dependent through the angles $\zeta(t)$ and $\psi(t)$ which define the direction of the dephasing vector (4). Furthermore, the second term in Eq. (14) is independent of $\psi$, while the third and the forth terms are harmonic functions of $\psi$ and $2\psi$, respectively (compare with Eq. (4) in [13]). To obtain isotropic diffusion weighting, expressed by Eq. (9), the corresponding integrals of the second, third and fourth terms in Eq. (14) must vanish. The condition for the second term of Eq. (14) to vanish upon integration leads to one possible solution for the angle $\zeta(t)$, i.e. the time-independent "magic angle"

$$\zeta_m = a\cos(1/\sqrt{3}). \tag{15}$$

By taking into account constant $\zeta_m$, the condition for the third and the fourth term in Eq. (14) to vanish upon integration is given by $$\int_0^{t_E} F(t)^2 \cos[2\psi(t)] dt = 0 \tag{16}$$

$$\int_0^{t_E} F(t)^2 \sin[2\psi(t)] dt = 0$$

$$\int_0^{t_E} F(t)^2 \cos[\psi(t)] dt = 0$$

$$\int_0^{t_E} F(t)^2 \sin[\psi(t)] dt = 0.$$

Conditions (16) can be rewritten in a more compact complex form as $$\int_0^{t_E} F(t)^2 \exp[ik\psi(t)] dt = 0, \tag{17}$$

which must be satisfied for k=1, 2. By introducing the rate $\dot{\tau}(t) = F(t)^2$, the integral (17) can be expressed with the new variable $\tau$ as $$\int_0^{t_d} \exp[ik\psi(\tau)] d\tau = 0. \tag{18}$$

Note that the upper integration boundary moved from $t_E$ to $t_d$. The condition (18) is satisfied when the period of the exponential is $t_d$, thus a solution for the azimuth angle is $$\psi(\tau) = \psi(0) + \frac{2\pi}{t_d} n\tau, \quad (19)$$

for any integer n other than 0. The time dependence of the azimuth angle is finally given by $$\psi(t) = \psi(0) + \frac{2\pi n}{t_d} \int_0^t F(t')^2 dt'. \quad (20)$$

The isotropic diffusion weighting scheme is thus determined by the dephasing vector q(t) with a normalized magnitude F(t) and a continuous orientation sweep through the angles $\zeta_m$(15) and $\psi$(t) (20). Note that since the isotropic weighting is invariant upon rotation of D, orientation of the vector q(t) and thus also orientation of the effective gradient g(t) can be arbitrarily offset relative to the laboratory frame in order to best suit the particular experimental conditions.

As understood from above, according to yet another specific embodiment, the isotropic diffusion weighting is achieved by a continuous sweep of the time-dependent dephasing vector q(t) where the azimuth angle $\psi$(t) and the magnitude thereof is a continuous function of time so that the time-dependent dephasing vector q(t) spans an entire range of orientations parallel to a right circular conical surface and so that the orientation of the time-dependent dephasing vector q(t) at time 0 is identical to the orientation at time $t_E$. Furthermore, according to yet another embodiment, the inclination $\zeta$ is chosen to be a constant, time-independent value, i.e. the so called magic angle, such that $\zeta = \zeta_m = a\cos(1/\sqrt{3})$.

The orientation of the dephasing vector, in the Cartesian coordinate system during the diffusion weighting sequence, spans the entire range of orientations parallel to the right circular conical surface with the aperture of the cone of $2*\zeta_m$ (double magic angle) and the orientation of the dephasing vector at time 0 is identical to the orientation of the dephasing vector at time $t_E$, i.e. $\psi(t_E)-\psi(0)=2*\pi*n$, where n is an integer (positive or negative, however not 0) and the absolute magnitude of the dephasing vector, q*F(t), is zero at time 0 and at time $t_E$. The isotropic weighting can also be achieved by q-modulations with discrete steps in azimuth angle $\psi$, providing q(t) vector steps through at least four orientations with unique values of $e^{i\psi}$, such that $\psi$ modulus $2\pi$ are equally spaced values. Choice of the consecutive order and duration of the time intervals during which $\psi$ is constant is arbitrary, provided that the magnitude F(t) is adjusted to meet the condition for isotropic weighing (10, 16).

Specific Implementations

The pulsed gradient spin-echo (PGSE) sequence with short pulses offers a simplest implementation of the isotropic weighting scheme according to the present invention. In PGSE, the short gradient pulses at times approximately 0 and $t_E$ cause the magnitude of the dephasing vector to instantaneously acquire its maximum value approximately at time 0 and vanish at time $t_E$. The normalized magnitude is in this case given simply by F(t)=1 in the interval $0<t<t_E$ and 0 otherwise, providing $t_d=t_E$. A simplest choice for the azimuth angle (20) is the one with n=1 and $\psi$(0)=0, thus $$\psi(t) = \frac{2\pi t}{t_E}. \quad (21)$$

The dephasing vector is given by $$q^T(t) = q\left\{\sqrt{\frac{2}{3}}\cos\left(\frac{2\pi t}{t_E}\right), \sqrt{\frac{2}{3}}\sin\left(\frac{2\pi t}{t_E}\right), \sqrt{\frac{1}{3}}\right\}. \quad (22)$$

The corresponding effective gradient, calculated from $$g^T(t) = \frac{1}{\gamma}\frac{d}{dt}q^T(t) \quad (23)$$

is $$g^T(t) = \frac{q}{\gamma}[\delta(0) - \delta(t_E)]\left\{\sqrt{\frac{2}{3}}, 0, \sqrt{\frac{1}{3}}\right\} + \quad (24)$$
$$\sqrt{\frac{2}{3}}\frac{2\pi}{t_E}\frac{q}{\gamma}\left\{-\sin\left(\frac{2\pi t}{t_E}\right), \cos\left(\frac{2\pi t}{t_E}\right), 0\right\}.$$

Here $\delta$(t) is the Dirac delta function. Rotation around the y-axis by a $\tan(\sqrt{2})$ yields $$g^T(t) = \frac{q}{\gamma}[\delta(0) - \delta(t_E)]\{0, 0, 1\} + \quad (25)$$
$$\sqrt{\frac{2}{3}}\frac{2\pi}{t_E}\frac{q}{\gamma}\left\{-\sqrt{\frac{1}{3}}\sin\left(\frac{2\pi t}{t_E}\right), \cos\left(\frac{2\pi t}{t_E}\right), -\sqrt{\frac{2}{3}}\sin\left(\frac{2\pi t}{t_E}\right)\right\}.$$

The effective gradient in Eqs. (24, 25) can conceptually be separated as the sum of two terms, $$g(t) = g_{PGSE}(t) + g_{iso}(t). \quad (26)$$

The first term, $g_{PGSE}$, represents the effective gradient in a regular PGSE two pulse sequence, while the second term, $g_{iso}$, might be called the "iso-pulse" since it is the effective gradient modulation which can be added to achieve isotropic weighting.

As may be seen from above, according to one specific embodiment of the present invention, the method is performed in a single shot, in which the latter should be understood to imply a single MR excitation.

The Analysis Method According to the Present Invention

Below the analysis method according to the present invention will be discussed in detail.

Fractional anisotropy (FA) is a well-established measure of anisotropy in diffusion MRI. FA is expressed as an invariant of the diffusion tensor with eigenvalues $\lambda_1$, $\lambda_2$ and $\lambda_3$, $$FA = \sqrt{\frac{(\lambda_1 - \lambda_2)^2 + (\lambda_1 - \lambda_3)^2 + (\lambda_2 - \lambda_3)^2}{2(\lambda_1^2 + \lambda_2^2 + \lambda_3^2)}}. \quad (27)$$

In typical diffusion MRI experiments, only a voxel average anisotropy can be detected. The sub-voxel microscopic anisotropy is often averaged out by a random distribution of main diffusion axis. Here we introduce a novel parameter for quantifying microscopic anisotropy and show how it can be determined by diffusion NMR.

Information about the degree of microscopic anisotropy can be obtained from comparison of the echo-attenuation curves, $E(b)=I(b)/I_0$, with and without the isotropic weighting. Multi-exponential echo attenuation is commonly observed in diffusion experiments. The multi exponential attenuation might be due to isotropic diffusion contributions, e.g. restricted diffusion with non-Gaussian diffusion, as well as due to the presence of multiple anisotropic domains with varying orientation of main diffusion axis. The inverse Laplace transform of E(b) provides a distribution of apparent diffusion coefficients P(D), with possibly overlapping isotropic and anisotropic contributions. However, in isotropically weighed diffusion experiments, the deviation from mono-exponential attenuation is expected to originate mainly from isotropic contributions.

In practice, the diffusion weighting b is often limited to a low-b regime, where only an initial deviation from mono-exponential attenuation may be observed. Such behaviour may be quantified in terms of the kurtosis coefficient K (Jensen, J. H., and Helpern, J. A. (2010). MRI quantification of non-Gaussian water diffusion by kurtosis analysis. NMR Biomed 23, 698-710.), $$\ln E = -\overline{D}b + \frac{\overline{D}^2 K}{6}b^2 - \dots \quad (28)$$

The second term in Eq. (28) can be expressed by the second central moment of the distribution P(D).

Provided that P(D) is normalized, $$\int_0^\infty P(D)dD = 1, \quad (29)$$

the normalized echo signal is given by the Laplace transform $$E(b) = \int_0^\infty P(D)e^{-bD}dD. \quad (30)$$

The distribution P(D) is completely determined by the mean value $$\overline{D} = \int_0^\infty DP(D)dD \quad (31)$$

and by the central moments $$\mu_m = \int_0^\infty (D - \overline{D})^m P(D)dD. \quad (32)$$

The second central moment gives the variance, $\mu_2 = \sigma^2$, while the third central moment, $\mu_3$, gives the skewness or asymmetry of the distribution P(D). On the other hand, the echo intensity can be expressed as a cumulant expansion (Frisken, B. (2001). Revisiting the method of cumulants for the analysis of dynamic light-scattering data. Appl Optics 40) by $$\ln E = -\overline{D}b + \frac{\mu_2}{2}b^2 - \dots \quad (33)$$

The first-order deviation from the mono-exponential decay is thus given by the variance of P(D).

Assuming diffusion tensors with axial symmetry, i.e. $\lambda_1 = D_\parallel$ and $\lambda_2 = \lambda_3 = D_\perp$, and an isotropic distribution of orientation of the tensor's main diffusion axis, the echo-signal E(b) and the corresponding distribution P(D) can be written in a simple form. In case of the single PGSE experiment, using a single diffusion encoding direction, the distribution is given by $$P(D) = \frac{1}{2\sqrt{(D - D_\perp)(D_\parallel - D_\perp)}}, \quad (34)$$

with the mean and variance, $$\overline{D} = \frac{D_\parallel + 2D_\perp}{3} \text{ and} \quad (35)$$

$$\mu_2 = \frac{4}{45}(D_\parallel - D_\perp)^2.$$

The echo-attenuation for the single PGSE is given by $$E(b) = \frac{\sqrt{\pi}}{2} \frac{e^{-bD_\perp}}{\sqrt{b(D_\parallel - D_\perp)}} \text{erf}\left(\sqrt{b(D_\parallel - D_\perp)}\right). \quad (36)$$

For a double PGSE with orthogonal encoding gradients, the distribution P(D) is given by $$P(D) = \frac{1}{\sqrt{(D_\parallel + D_\perp - 2D)(D_\parallel - D_\perp)}}, \quad (37)$$

with the same mean value as for the single PGSE but with a reduced variance, $$\mu_2 = \frac{1}{45}(D_\perp - D_\parallel)^2. \quad (38)$$

As in the single PGSE, also in double PGSE the echo-attenuation exhibits multi-component decay, $$E(b) = \frac{\sqrt{\pi}}{2} \frac{e^{-b\frac{D_\perp + D_\parallel}{2}}}{\sqrt{b\frac{D_\perp - D_\parallel}{2}}} \text{erf}\left(\sqrt{b\frac{D_\perp - D_\parallel}{2}}\right). \quad (39)$$

For randomly oriented anisotropic domains, the non-isotropic diffusion weighting results in a relatively broad distribution of diffusion coefficients, although reduced four-fold when measured with a double PGSE compared to the single PGSE. On the other hand the isotropic weighting results in $$P(D) = \delta\left(D - \frac{D_\parallel + 2D_\perp}{3}\right), \quad (40)$$

with $$\mu_2 = 0 \quad (41)$$

and a mono-exponential signal decay $$E(b) = e^{-b\overline{D}}. \tag{42}$$

The variance $\mu_2$ could be estimated by applying a function of the form (33) to fitting the echo attenuation data. However, in case of randomly oriented anisotropic domains, the convergence of the cumulant expansion of (36) is slow, thus several cumulants may be needed to adequately describe the echo attenuation (36). Alternatively, the distribution (34) may be approximated with the Gamma distribution $$P(D) = D^{\alpha-1} \frac{e^{-D/\beta}}{\Gamma(\alpha)\beta^\alpha}, \tag{43}$$

where $\alpha$ is known as the shape parameter and $\beta$ is known as the scale parameter. For the Gamma distribution, the mean diffusivity is given by $\overline{D} = \alpha \cdot \beta$, while the variance is given by $\mu_2 = \alpha \cdot \beta^2$. The Gamma distribution is an efficient fitting function. With the two parameters it can capture a wide range of diffusion distributions, with both isotropic as well as anisotropic contributions. Conveniently, the Laplace transform of the Gamma function takes a simple analytical form, $$E(b) = (1 + b\beta)^{-\alpha} = \left(1 + b\frac{\mu_2}{\overline{D}}\right)^{-\frac{\overline{D}^2}{\mu_2}}. \tag{44}$$

The variance, $\mu_2^{iso}$, obtained by fitting the function (44) to the isotropic diffusion weighted echo-decay is related to the isotropic diffusion contributions, since the variance is expected to vanish with isotropic weighting in a pure microscopically anisotropic system (see Eq. 41). The same fitting procedure on non-isotropically weighted data will yield the variance $\mu_2$ due to both isotropic and anisotropic contributions. The difference $\mu_2 - \mu_2^{iso}$ vanishes when all diffusion contributions are isotropic and therefore provides a measure of microscopic anisotropy. The mean diffusivity $\overline{D}$, on the other hand, is expected to be identical for both isotropically and non-isotropically weighted data. The difference $\mu_2 - \mu_2^{iso}$ is thus obtained by using the $\mu_2^{iso}$ and $\mu_2$ as free fit parameters when Eq. (44) is fitted to isotropically and non-isotropically weighted data sets, respectively, while a common parameter $\overline{D}$ is used to fit both data sets.

The difference $\mu_2 - \mu_2^{iso}$ along with $\overline{D}$ provide a novel measure for the microscopic fractional anisotropy ($\mu FA$) as $$\mu FA = \sqrt{\frac{3}{2}} \sqrt{\frac{\mu_2 - \mu_2^{iso}}{\mu_2 - \mu_2^{iso} + 2\overline{D}^2/5}}. \tag{45}$$

The $\mu FA$ is defined so that the $\mu FA$ values correspond to the values of the well-established FA when diffusion is locally purely anisotropic and determined by randomly oriented axially symmetric diffusion tensors with identical eigenvalues. Eq. (45) is obtained by setting $\mu FA = FA$ (27), assuming $\mu_2 - \mu_2^{iso} = \mu_2$ and expressing the eigenvalues $D_\parallel$ and $D_\perp$ in terms of $\overline{D}$ and $\mu_2$ (see Eq. 35). In the case of a one-dimensional curvilinear diffusion, when $D_\parallel \gg D_\perp$, $\mu FA = FA = 1$ and in the case of two-dimensional curvilinear diffusion, when $D_\parallel \ll D_\perp$, $\mu FA = FA = 1/\sqrt{2}$.

The difference $\mu_2 - \mu_2^{iso}$ in Eq. (45) ensures that the microscopic anisotropy can be quantified even when isotropic diffusion components are present. Isotropic restrictions, e.g. spherical cells, characterised by non-Gaussian restricted diffusion, are expected to cause a relative increase of both $\mu_2$ and $\mu_2^{iso}$ by the same amount, thus providing the difference $\mu_2 - \mu_2^{iso}$ independent of the amount of isotropic contributions. The amount of non-Gaussian contributions could be quantified for example as the ratio $\sqrt{\mu_2^{iso}}/\overline{D}$ For anisotropic diffusion with finite orientation dispersion, i.e. when local diffusion tensors are not completely randomly oriented, the $\overline{D}$ and $\mu_2 - \mu_2^{iso}$ are expected to depend on the gradient orientation in the non-isotropic diffusion weighting experiment. Furthermore, variation of the apparent diffusion coefficient (ADC), i.e. volume weighted average diffusivity, dependent on the gradient orientation and given by the initial echo decay of the non-isotropic diffusion weighting experiment, may indicate a finite orientation dispersion. Non-isotropic weighting experiment performed in several directions, similar to the diffusion tensor and diffusion kurtosis tensor measurements, performed with a range of b values to detect possibly multi-exponential decays, combined with the isotropic weighting experiment, is thus expected to yield additional information about microscopic anisotropy as well as information related to the orientation dispersion of anisotropic domains.

Eq. (44) could be expanded by additional terms in cases where this is appropriate. For example, the effects of a distinct signal contribution by the cerebrospinal fluid (CSF) in brain could be described by adding a mono-exponential term with the isotropic CSF diffusivity $D_1$ to Eq. (44), $$E(b) = fe^{-bD_1} + (1-f)\left(1 + b\frac{\mu_2}{\overline{D}}\right)^{-\frac{\overline{D}^2}{\mu_2}}, \tag{46}$$

where f is the fraction of the additional signal contribution. Eq. (46) could be used instead of Eq. (44) to fit the experimental data.

A further explanation directed to inter alia $\mu FA$ estimation and optimal range of the diffusion weighting b is given below in the section describing the figures in more detail.

In relation to the description above and below it should be mentioned that also multi-echo variants of course are possible according to the present invention. Such may in some cases be benefitial for flow/motion compensation and for compensation of possible assymetry in gradient generating equipment.

Specific Embodiments of the Present Invention

Below, specific embodiments of the analysis method according to the present invention will be disclosed. According to one specific embodiment, the method involves approximating the distribution of apparent diffusion coefficients by using a Gamma distribution and the signal attenuation by its inverse Laplace transform. This may increase the speed of the fitting procedure discussed below. The distribution of diffusion coefficients may contain isotropic and/or anisotropic contributions, it may arise due to a distribution of Gaussian diffusion contributions or it may be a consequence of a non-Gaussian nature of diffusion, e.g. restricted diffusion, or it may be due to orientation dispersion of anisotropic diffusion contributions (randomly oriented diffusion tensors) or it may be due to a combination of the above.

One of the main advantages of the analysis method according to the present invention is that it can quantify degree of microscopic anisotropy with high precision from low b-range signal intensity data even in the presence of isotropic contributions, i.e. when they cause deviation from mono-exponential decay. Typically, isotropic contributions would bias the quantification of anisotropy from single PGSE attenuation curves, because multi-exponential signal decays due to isotropic contributions may look similar or indistinguishable to the ones caused by anisotropic contributions. The analysis according to the present invention allows to separate the influence of anisotropic diffusion contributions from the influence of isotropic diffusion contributions on the first order deviation from the mono-exponential decays, where the first order deviation may be referred to as diffusion kurtosis or the second central moment of diffusion distribution, and therefore allows for quantification of the degree of microscopic anisotropy. Therefore, according to the present invention, the method may involve using a fit function (44) comprising the parameters: initial value $$\left(I_0 = \lim_{b \to 0} I(b)\right),$$

initial slope $$\left(\overline{D} = -\lim_{b \to 0} \frac{\partial}{\partial b} \ln\left(\frac{I(b)}{I_0}\right)\right),$$

i.e. the volume weighted average diffusivity or the mean diffusivity of a diffusion tensor $\overline{D}$) and curvature, i.e. the second central moment of diffusion distribution ($\mu_2$). See Eq. (44). Note that $E(b)=I(b)/I_0$. Therefore, according to one specific embodiment of the present invention, the two acquired echo attenuation curves (log E vs. b, where E is echo amplitude, which may be normalized, and b is the diffusion weighting factor) are compared in terms of initial value, initial slope or curvature, and/or the ratio between the two echo attenuation curves is determined, so that the degree of microscopic anisotropy may be determined.

The method may involve fitting the isotropic and non-isotropic weighted data with the fit function (44) comprising the parameters: initial values $$\left(I_0 = \lim_{b \to 0} I(b)\right)$$

for isotropic and non-isotropic data, initial slope $$\left(\overline{D} = -\lim_{b \to 0} \frac{\partial}{\partial b} \ln\left(\frac{I(b)}{I_0}\right)\right),$$

i.e. the volume weighted average diffusivity or the mean diffusivity of a diffusion tensor $\overline{D}$) with constraint that $\overline{D}$ values are identical for both isotropic and non-isotropic diffusion weighted data and the second central moments, $\mu_2^{iso}$ and $\mu_2$ for isotropic and non-isotropic diffusion weighted data, respectively. The microscopic fractional anisotropy ($\mu FA$) is then calculated from the mean diffusivity, $\overline{D}$, and the second central moments of diffusion distribution, $\mu_2^{iso}$ and $\mu_2$ according to Eq. (45). As disclosed above, according to one embodiment a fit function comprising the parameters initial value, initial slope and curvature (zeroth, first, and second central moment of the probability distribution of diffusion coefficients), fraction of the additional diffusion contribution (f) and/or diffusivity of the additional contribution ($D_1$) (see discussion below) are used. When the extended fitting model described in Eq. (46) is applied, then the mean diffusivity, $\overline{D}$, the additional diffusion contribution (f) and the diffusivity of the additional contribution ($D_1$) are constrained to be equal for the isotropic and the non-isotropic diffusion weighted data.

Moreover, according to another embodiment of the present invention, the microscopic fractional anisotropy ($\mu FA$) is calculated from mean diffusivity ($\overline{D}$) and difference in second central moments of diffusion distribution ($\mu_2^{iso}$ and $\mu_2$).

The method may also involve fitting the isotropic and non-isotropic weighted data, where non-isotropic weighted data is acquired separately for several directions of the magnetic field gradients with the fit function (44) comprising the parameters: initial value $$\left(I_0 = \lim_{b \to 0} I(b)\right),$$

initial slope $$\left(\overline{D}_g = -\lim_{b \to 0} \frac{\partial}{\partial b} \ln\left(\frac{I(b)}{I_0}\right)\right),$$

i.e. the volume weighted average diffusivity $\overline{D}_g$ generally depending on the gradient orientation) and curvature, i.e. the second central moment of diffusion distribution ($\mu_2$). Different fit constraints may be applied to optimize the accuracy of the estimated fit parameters. For example, the, initial slope ($\overline{D}_g$), i.e. the volume weighted average diffusivity $\overline{D}_g$ estimated from the non-isotropic diffusion weighted data acquired with diffusion weighting in different directions, such to yield information required to construct the diffusion tensor, D, could be subjected to the constraint where the trace of the diffusion tensor (determined by non-isotropic diffusion weighting experiments) is identical to three times the mean diffusivity, $\overline{D}$, obtained from the isotropic diffusion weighting data, i.e. $tr(D)=3\overline{D}$. In such a case, the microscopic fractional anisotropy ($\mu FA$) parameter could still be calculated according to Eq. (45), however, care need to be taken when interpreting results of such calculations. As an alternative to fitting the non-isotropic diffusion weighted data in different gradient directions, e.g. from diffusion tensor measurement, the signal intensities may be averaged across the gradient orientations. The resulting curve will approximate a sample having full orientation dispersion, since averaging under varying gradient orientations is identical to averaging under varying orientations of the object. Therefore, according to one specific embodiment of the present invention, the echo attenuation curves acquired with at least one of the gradient modulation scheme based on isotropic diffusion weighting and the gradient modulation scheme based on non-isotropic diffusion weighting are averaged across multiple encoding directions.

The method may involve the use of additional terms in Eq. (44), such as Eq. (46), applied to the analysis described in the above paragraphs. Eq. (46) comprises two additional parameters, i.e. fraction of the additional diffusion contribution (f) and diffusivity of the additional contribution ($D_1$). One such example may be the analysis of data from the human brain, where the additional term in Eq. (46) could be assigned to the signal from the cerebrospinal fluid (CSF). The parameter $\overline{D}$ in Eq. (46) would in this case be assigned to the mean diffusivity in tissue while the parameter $D_1$ would be assigned to the diffusivity of the CSF. The isotropic diffusion weighting could thus be used to obtain the mean diffusivity in the brain tissue without the contribution of the CSF.

In addition, valuable information about anisotropy may be obtained from the ratio of the non-isotropically and the isotropically weighted signal or their logarithms. For example, the ratio of the non-isotropically and the isotropically weighted signals at intermediate b-values, might be used to estimate the difference between the radial ($D_⊥$) and the axial ($D_∥$) diffusivity in the human brain tissue due to the diffusion restriction effect by the axons. Extracting the information about microscopic anisotropy from the ratio of the signals might be advantageous, because the isotropic components with high diffusivity, e.g. due to the CSF, are suppressed at higher b-values. Such a signal ratio or any parameters derived from it might be used for generating parameter maps in MRI or for generating MR image contrast.

It is interesting to note that the μFA parameter is complementary to the FA parameter, in the sense that μFA can be finite in cases when FA=0, while, on the other hand, μFA tends to vanish when FA is maximized by anisotropy on the macroscopic scale. Such approach could be used to analyse microscopic anisotropy and orientation distribution in a similar way as the diffusion tensor and kurtosis tensor analysis is used. Compared to the kurtosis tensor analysis, here presented microscopic fractional anisotropy analysis is advantageous in that it can separate the isotropic diffusion components that may contribute to the values of kurtosis detected with the present methodology for kurtosis tensor measurements.

The analysis method according to the present invention is applicable in many different situations. According to one embodiment, the method is performed so that mean diffusivity is constrained to be identical for both isotropic and non-isotropic diffusion weighted data. If Eq. (46) is employed, then parameters f and $D_1$ are also constrained to be equal for isotropic and non-isotropic diffusion weighted data. Furthermore, according to another specific embodiment of the present invention, the echo attention curve acquired with the gradient modulation scheme based on isotropic diffusion is assumed to be monoexponential. This may be of interest for the sake of approximating the microscopic anisotropy.

According to another embodiment, the method is performed so that a mean diffusivity for isotropic diffusion weighted data is allowed to be different from the mean diffusivity for non-isotropic diffusion weighted data. This latter case would be better in cases when the micro-domains do not have random orientations, i.e. orientation dispersion is not isotropic. In such cases the mean diffusivity depends on orientation of the non-isotropic weighting. The analysis method according to the present invention may involve different forms of experiments. In this sense it should be noted that the present analysis encompasses all diffusion weighting pulse sequences where one achieves isotropic diffusion weighting and the other with a non-isotropic diffusion weighting. According to the present invention, there are however some specific set-up alternatives that may be mentioned additionally. According to one specific embodiment, the isotropic diffusion weighting and the non-isotropic diffusion weighting is achieved by two different pulse gradient spin echos (PGSEs). According to one specific embodiment of the present invention, the gradient modulation scheme based on isotropic diffusion weighting comprises at least one harmonically modulated gradient, which removes curvature of log E vs. b originating from anisotropy. According to yet another embodiment, the method involves a single-PGSE yielding maximum curvature of log E vs. b for the non-isotropic diffusion weighting, and a single-PGSE augmented with sinusoidal isotropic gradients for the isotropic diffusion weighting.

As discussed above and shown in FIGS. 1A-C and e.g. 2A-C, the analysis method according to the present invention may be performed on many different forms of materials and substances. According to one specific embodiment of the present invention, the method allows for determining the degree of anisotropy in systems with anisotropic and/or isotropic diffusion, such as in liquid crystals. This may be used to infer about the geometry of micro-domains. For example, the analysis may be used to identify cases of curvilinear diffusion in 1D with highest microscopic anisotropy (μFA=1) or in 2D when diffusion is restricted to domains with planar geometry (μFA=1/√2), and other intermediate cases between isotropic and 1D diffusion. As may be understood, the present invention also encompasses use of an analysis method as disclosed above. According to one specific embodiment, the present invention provides use of the analysis method, for yielding an estimate of the microscopic fractional anisotropy (μFA) with a value for quantifying anisotropy on the microscopic scale. Furthermore, there is also provided the use of a method according to the present invention, wherein anyone of the parameters microscopic fractional anisotropy (μFA), mean diffusivity ($\overline{D}$), $\sqrt{\mu_2^{iso}}/\overline{D}$, fraction of the additional diffusion contribution (f) and/or diffusivity of the additional contribution ($D_1$) or any other parameter(s) calculated from $\mu_2$, $\mu_2^{iso}$ or mean diffusivity is used for generating parameter maps in MRI or for generating MR image contrast. Information about microscopic diffusivity may be obtained from the ratio of the non-isotropically and isotropically weighted signals or their logarithms and may be used in parameter maps in MRI or for generating MR image contrast. The difference between the radial and axial diffusivity may be extracted (see above), which is obtained from the ratio of the signals.

Furthermore, intended is also the use of a method according to the present invention, wherein microscopic fractional anisotropy (μFA) is used for characterizing tissue and/or diagnosing, such as for diagnosing a tumour disease or other brain or neurological disorders.

Moreover, also as hinted above, the analysis method according to the present invention may also be coupled to a pre-performed method involving isotropic and non-isotropic diffusion weighting.

DETAILED DESCRIPTION OF THE DRAWINGS

In FIG. 1A-C there is shown a schematic representation of signal decays vs. b for isotropic and non-isotropic diffusion weighting for different types of materials. In FIG. 1 the following is valid: A) Solid lines represent decays in a non-isotropic diffusion weighting experiment for 1D and 2D curvilinear diffusion (e.g. diffusion in reversed hexagonal phase H2 (tubes) and in lamellar phase Lα (planes), respectively). Dashed lines are the corresponding decays with isotropic diffusion weighting. The initial decay ($\overline{D}$) is identical for the isotropic diffusion weighting as for the non-isotropic diffusion weighting. B) The decay for a system with 70% free isotropic diffusion and 30% restricted isotropic diffusion. In this case the isotropic and non-isotropic diffusion weighting result in identical signal decays in the entire b-range. C) Decays for a system with 70% anisotropic diffusion (2D) and 30% restricted isotropic diffusion. Solid line corresponds to the non-isotropic diffusion weighting while the dashed line corresponds to the isotropic diffusion weighting. The initial decays are identical for the isotropic and for the non-isotropic diffusion weighting, while the deviation between the decays at higher b values reveals the degree of anisotropy.

In relation to the analysis performed and the presented results it may also be mentioned that comparing the signal decays of the two acquired echo attenuation curves may involve analysis of the ratio and/or difference between the two acquired echo attenuation curves.

In FIG. 2A-C are shown experimental results with analysis of micro-anisotropy for different types of materials. Shown are normalized signal decays vs. $b\overline{D}$ for isotropic (circles) and non-isotropic (crosses) diffusion weighting. Solid lines represent optimal fits of Eq. (44) to the experimental data, with constraint of equal initial decays, $\overline{D}$, (shown as dashed lines) for isotropic and non-isotropic weighted data. All experiments were performed at 25° C. In all experiments, signal intensities were obtained by integration of the water peak. A) free water; data from the isotropic and non-isotropic diffusion weighting overlap and give rise to mono-exponential signal decays. The analysis gives $\overline{D}=2.2\times10^{-9}$ m$^2$/s and µLFA=0. B) Suspension of yeast cells from baker's yeast (Jästbolaget AB, Sweden) in tap water with restricted water diffusion; data from the isotropic and non-isotropic diffusion weighting overlap and give rise to multi-exponential signal decays. The analysis gives $\overline{D}=1.4\times10^{-9}$ m$^2$/s and µLFA=0. C) Diffusion of water in a liquid crystal material composed by the Pluronic surfactant E5P68E6 with very high microscopic anisotropy, corresponding to a reverse hexagonal phase; data from the isotropic and non-isotropic diffusion weighting diverge at higher b-values and give rise to multi-exponential signal decay in case of the non-isotropic diffusion weighting and mono-exponential signal decay in case of the isotropic diffusion weighting. The analysis gives $\overline{D}=4.8\times10^{-10}$ m$^2$/s and µLFA=1.0.

Figure 3B:
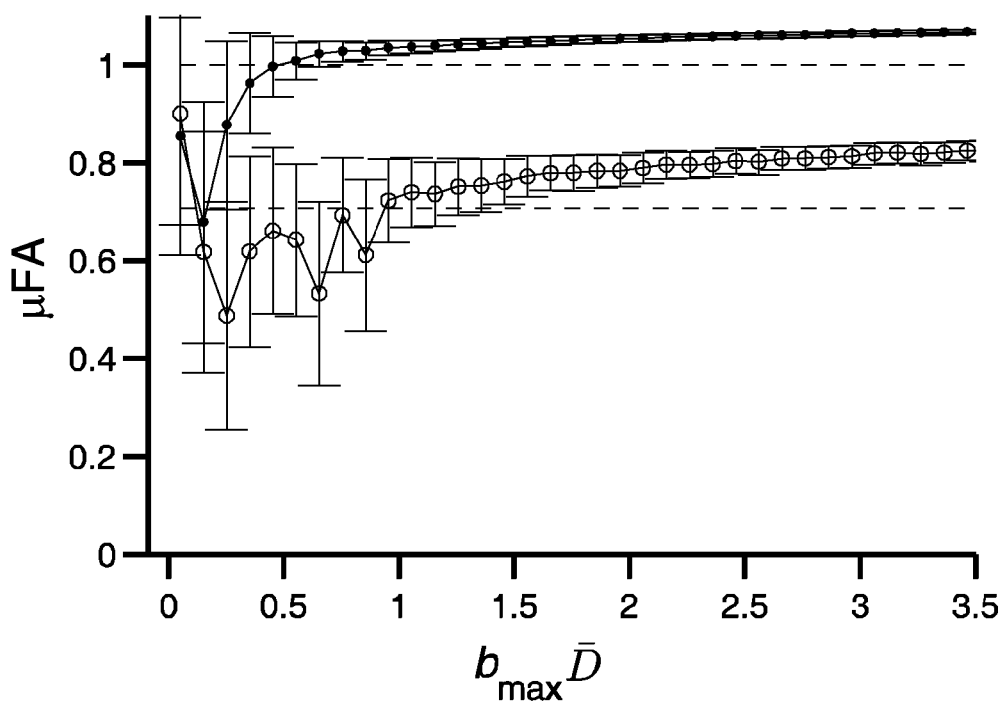

In FIGS. 3A and 3B, the results of the Monte-Carlo error analysis show systematic deviations and precision of the $\overline{D}$ (A) and µFA (B) parameters estimated for the 1D (dots) and 2D (circles) curvilinear diffusion according to what has been disclosed above. The ratio of the estimated mean diffusivity to the exact values $\overline{D}$, labelled as $D/\overline{D}$ (A) with the corresponding standard deviation values and the estimated µFA values (B) with the corresponding standard deviations are shown as dots/circles and error bars, respectively, as a function of the maximum attenuation factor $b_{max}\overline{D}$ for signal to noise level of 30.

For µFA estimation, the optimal choice of the b-values is important. To investigate the optimal range of b-values, a Monte-Carlo error analysis depicted in FIGS. 3A and 3B has been performed. The echo-signal was generated as a function 16 equally spaced b-values between 0 and $b_{max}$ for the cases of 1D and 2D curvilinear diffusion with randomly oriented domains. The upper limit, $b_{max}$, was varied and the attenuation factors $b\overline{D}$ were chosen to be identical for the 1D and 2D case. The signal was subjected to the Rician noise with a constant signal to noise, SNR=30, determined relative to the non-weighted signal. Isotropic and non-isotropic weighed attenuation data were analyzed with the protocol described herein to obtain $\overline{D}$ and µFA parameters. This analysis was repeated in 1000 iterations by adding different simulated noise signals with the given SNR. The procedure yields the mean and the standard deviation of the estimated $\overline{D}$ and µFA, shown as dots/circles and error bars respectively in FIG. 3B.

The optimal range of the diffusion weighting b is given by a compromise between accuracy and precision of the µFA analysis and it depends on the mean diffusivity. If the maximum b value used is lower than $1/\overline{D}$, the µFA tends to be underestimated, while for maximum b values larger than $1/\overline{D}$ the µFA tends to be overestimated. On the other hand the accuracy of µFA is compromised particularly at too low values of the maximum b, due to increased sensitivity to noise. See FIG. 3B.

The invention claimed is:

1. Method for detecting microscopic diffusion anisotropy in a material, the method comprising:
performing an NMR and/or MRI experiment on the material to
acquire isotropically diffusion weighted echo attenuation data using a gradient modulation scheme causing an isotropic diffusion weighting of signal attenuation, such that the isotropic diffusion weighting in the material is invariant under rotation of the material, and
acquire non-isotropically diffusion weighted echo attenuation data using a gradient modulation scheme causing a non-isotropic weighting of signal attenuation,
wherein the performing includes generating RF and magnetic gradient sequences and measuring signals received from the material based on the generated RF and magnetic gradient sequences,
fitting a respective echo attenuation curve E(b), wherein E is an echo amplitude and b is a diffusion weighting factor, to the acquired isotropically diffusion weighted echo attenuation data and to the acquired non-isotropically diffusion weighted echo attenuation data, and
analysing said echo attenuation curves E(b) by comparing the signal decays of said echo attenuation curves to determine a difference between the signal decays, wherein the difference between the signal decays indicates microscopic diffusion anisotropy in the material.

2. Method according to claim 1, wherein isotropically diffusion weighted echo attenuation data or the non-isotropically diffusion weighted echo attenuation data is averaged across multiple encoding directions.

3. Method according to claim 1, wherein comparing the signal decays of said echo attenuation curves involves analysis of a ratio and/or a difference between parameters derived from the two acquired echo attenuation curves.

4. Method according to claim 1, wherein the echo attenuation curves are compared in terms of initial value, initial slope or curvature, and/or the ratio between echo amplitudes of the echo attenuation curves is determined, so that a degree of microscopic anisotropy may be determined.

5. Method according to claim 1, wherein a respective fit function comprising a parameters initial value, initial slope and curvature, the curvature given by a zeroth, a first and/or a second central moment of a probability distribution of diffusion coefficients, fraction of an additional diffusion contribution (f) and/or diffusivity of an additional contribution ($D_1$), is fitted to said isotropically diffusion weighted echo attenuation and non-isotropically diffusion weighted echo attenuation.

6. Method according to claim 1, wherein the isotropically diffusion weighted echo attenuation data acquired with the gradient modulation scheme based on isotropic diffusion is assumed to be monoexponential.

7. Method according to claim 1, wherein microscopic fractional anisotropy (µFA) is calculated from a mean diffusivity ($\overline{D}$) and a difference in second central moments $\mu_2^{iso}$ and $\mu_2$ of distributions of diffusion coefficients.

8. Method according to claim 1, wherein the method involves approximating a distribution of apparent diffusion coefficients by using a Gamma distribution and a signal attenuation by its Laplace transform.

9. Method according to claim 1, wherein the method is performed so that mean diffusivity is constrained to be identical for both isotropic and non-isotropic diffusion weighted data.

10. Method according to claim 1, wherein the method is performed so that mean diffusivity for isotropic diffusion weighted data is allowed to be different from mean diffusivity for non-isotropic diffusion weighted data.

11. Method according to claim 1, wherein the isotropic diffusion weighting and the non-isotropic diffusion weighting is achieved by two different pulse gradient spin echos (PGSEs).

12. Method according to claim 1, wherein the gradient modulation scheme based on isotropic diffusion weighting comprises at least one harmonically modulated gradient, which removes curvature of log E vs. b originating from anisotropy.

13. Method according to claim 1, wherein the method involves a single-PGSE yielding maximum curvature of log E vs. b for the non-isotropic diffusion weighting, and a single-PGSE augmented with sinusoidal isotropic gradients for the isotropic diffusion weighting.

* * * * *